United States Patent [19]

Elam

[11] 4,449,526
[45] May 22, 1984

[54] MASK BREATHING SYSTEM

[76] Inventor: James O. Elam, 1822 Canelo St., Dallas, Tex. 75323

[21] Appl. No.: 325,259

[22] Filed: Nov. 27, 1981

[51] Int. Cl.³ .............................................. A61M 16/00
[52] U.S. Cl. ........................... 128/206.21; 128/201.18; 128/206.24; 128/206.26; 128/207.14
[58] Field of Search .............. 128/136, 200.26, 201.18, 128/201.26, 202.28, 206.26, 206.29, 207.14, 207.15, 207.16, 207.17, 206.21, 206.24, 206.28; 604/170, 45, 281, 43, 35

[56] References Cited

U.S. PATENT DOCUMENTS

| 42,721 | 5/1864 | Albee | 128/206.26 |
|---|---|---|---|
| 1,050,620 | 1/1913 | De Ford | 128/206.29 |
| 1,786,350 | 12/1930 | Lambert | 128/207.14 |
| 2,393,002 | 1/1946 | Smith | 604/43 |
| 2,857,911 | 10/1958 | Bennett | 128/206.24 |
| 2,862,498 | 12/1958 | Weekes | 128/207.14 |
| 3,060,927 | 10/1962 | Gattone | 128/202.28 |
| 3,137,293 | 6/1964 | Green | 128/202.28 |
| 3,363,629 | 1/1968 | Kuhn | 128/207.15 |
| 3,982,532 | 9/1976 | Halldin et al. | 128/206.24 |
| 4,030,493 | 6/1977 | Walters et al. | 128/206.21 |
| 4,240,420 | 12/1980 | Riaboy | 128/206.14 |
| 4,300,550 | 11/1981 | Gandi et al. | 604/35 |
| 4,305,387 | 12/1981 | Reist-Kundig et al. | 128/206.26 |

FOREIGN PATENT DOCUMENTS

| 669841 | 1/1939 | Fed. Rep. of Germany | 128/201.18 |
|---|---|---|---|
| 23063 | 4/1962 | German Democratic Rep. | 128/206.29 |

Primary Examiner—Henry J. Recla
Assistant Examiner—Karin M. Reichle
Attorney, Agent, or Firm—Arnstein, Gluck, Lehr, Barron & Milligan

[57] ABSTRACT

A mouth mask includes a unitary member having an inner wall portion and an outer wall portion. The unitary member is adapted to seal about the lips of a patient with the perimeter defined by the intersection of the inner and outer wall portions resting on the perioral area overlying the maxilla and mandible. The mouth mask also includes an opening extending through the unitary member for connecting oxygen and ventilating through a mouthpiece or pharyngeal airway inserted through the opening in the mouth mask. The opening is adapted to receive an airway having a proximal end disposed externally of the patient and a distal end disposed internally of the patient in the region of the lower pharynx. Additionally, the mouth mask may selectively be provided with a nostril occluding balloon or cushion to pneumatically seal and block the nostrils of the patient.

43 Claims, 24 Drawing Figures

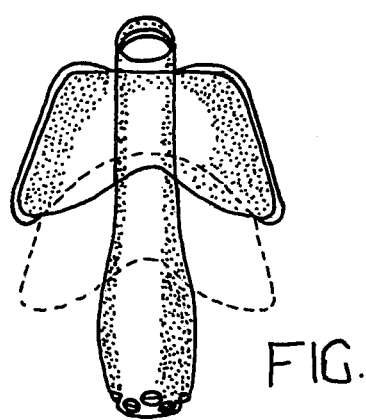
FIG. 7
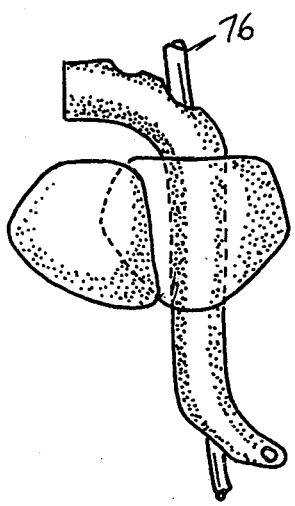
FIG. 8
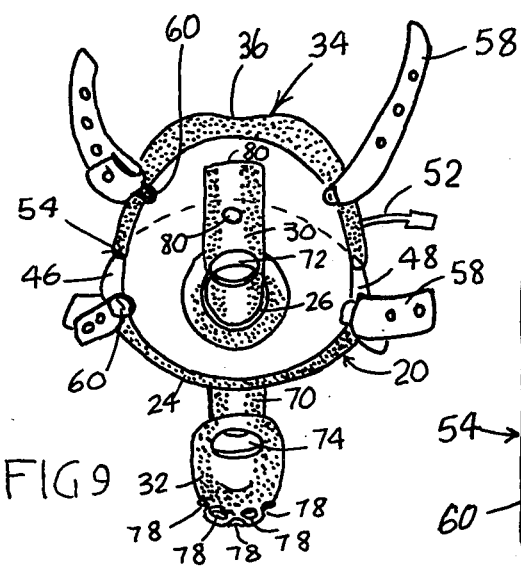
FIG 9
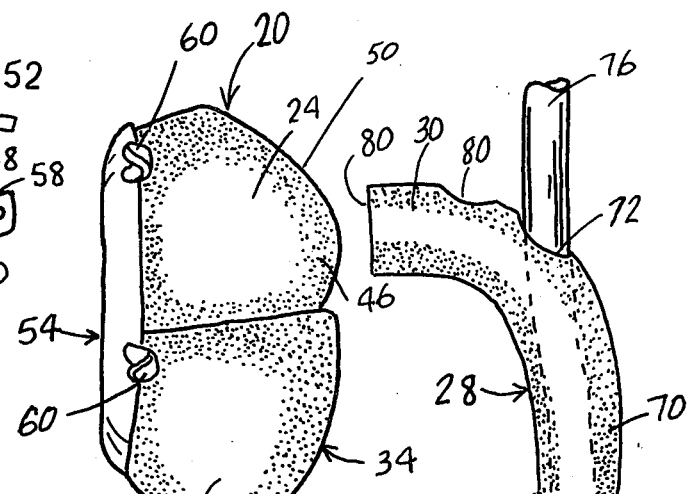
FIG. 10
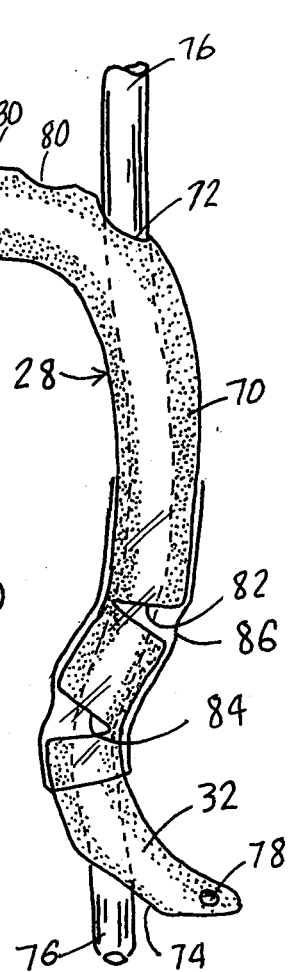
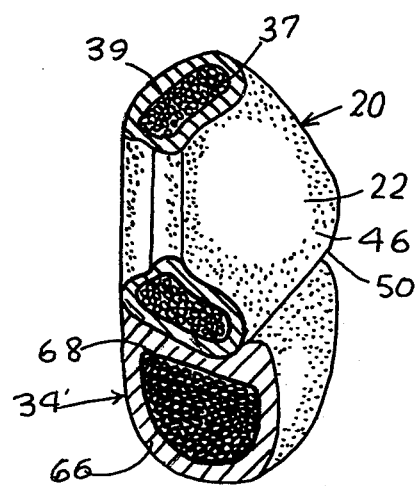
FIG. 11

MASK BREATHING SYSTEM

BACKGROUND OF THE INVENTION

The present invention relates to mouth masks and, more particularly, to mouth masks with improved versatility and safety features.

At present, there is an enormous gap in the prevailing methodologies by which non-anesthesia personnel attempt to manage ventilation and upper airway control. While some paramedics, emergency room physicians and nurses who are experienced in cardiopulmonary resuscitation (CPR) cases employ endotracheal intubation, other rescuers of minimal training either cannot intubate the trachea or are forbidden to do so. Moreover, there is little opportunity for improving the capability of inexperienced or untrained rescuers resulting in the unavailability of sufficiently trained or supervised rescuers.

Specifically, the neophyte rescuer must improvise upper airway management with various manual maneuvers by using devices such as oral airways and face masks. Unfortunately, these devices have remained basically unchanged since their introduction in the era of 1850 to 1910, despite the compelling need for improved devices of this type which are suitable not only for emergency room physicians but for rescuers of minimal training, as well. When the casual rescuer attempts to ventilate an unconscious apneic collapsed human, whose stomach is filled with strong acid, available oral airways and face masks do not assure against lethal complications such as regurgitation of gastric acid and pulmonary aspiration that can later asphyxiate the resuscitated patient.

With conventional oral airways and face masks, pharyngeal secretions cannot be removed without interrupting ventilation. This form of airway movement is often complex and difficult for non-anesthesia personnel when the airway is filled with secretions or blood so that means need to be found which minimize the potential complications of apnea asphyxia and chemical pneumonia. Moreover, conventional face masks have long presented problems of concern because of poor fit on edentulous and otherwise unusual facial contours.

In particular, it is difficult to attempt to seal the oral and nasal perimeter with conventional face masks because of the remarkable range of variability in both dimensions and contours of the adult human. The inability to provide the needed seal results in leakage during lung inflation which challenges the fit of any mask in certain patients. Additionally, the head straps commonly associated with conventional face masks may be abused by strapping too tight thereby producing prolonged ischemic pressure and skin necrosis in the orbital-nasal bridge area.

Today, a plethora of shapes and sizes are available in oronasal masks which attempt to fit the large variety of facial contours. For instance, as few as three and as many as eight different masks must be kept available. As a result, a need has remained for a significantly improved face mask capable of use substantially independently of the facial contour variations.

It is therefore an object of the present invention to provide a mouth mask adapted to seal around the widely opened mouth of a patient.

Another object of the present invention is to provide a mouth mask of the type described which rests on the perioral area overlying the maxilla and mandible.

Still another object of the present invention is to design a mask structure which inherently conforms to the patient's perioral area leak-free without traumatically high pressure of application by virtue of a broad contact surface.

Still a further object of the present invention is to provide a mouth mask of the type described adapted to selectively cooperate with a nostril occluding balloon or cushion to pneumatically seal the nostrils of a patient.

An additional object of the present invention is to provide a mouth mask and airway of the types described suited for use by emergency room physicians and nurses and neophyte rescuers alike.

Still an additional object of the present invention is to provide a mouth mask and airway of the types described providing accessibility through ports for suctioning secretions without breaking the seal of the mask or interrupting oxygenation.

Yet another object of the present invention is to provide a mouth mask and airway of the types described providing assurances against passage of an esophageal catheter into the trachea by reason of the airway structure.

Yet a further object of the present invention is to provide a mouth mask and airway of the types described providing optional modification giving a wide range of anterior/posterior adjustment to accommodate the variations in patient anatomies.

Still another object of the present invention is to provide a mouth mask and airway of the types described capable of overcoming the problems inherent in conventional oral airways and face masks.

These and other objects, advantages and features of the present invention will become apparent from the following description when taken in conjunction with the accompanying drawings.

SUMMARY OF THE INVENTION

In general, the objects and advantages of the present invention are met by providing an improved mouth mask in the form of a unitary member having an inner wall and an outer wall. The unitary member is adapted to seal about the lips of a patient with the perimeter defined by the intersection of the inner and outer wall portions resting on the perioral area overlying the maxilla and mandible. The mouth mask also includes an opening extending through the unitary member for placing a mouthpiece or airway through the unitary member for managing the patient's upper airway. The opening is adapted to receive a tube having a proximal end disposed externally of the patient and a distal end disposed internally of the patient in the region of the lower pharynx. Additionally, the mouth mask may selectively be provided with a nostril occluding balloon or cushion to pneumatically seal and block the nostrils of the patient.

BRIEF DESCRIPTION OF THE DRAWINGS

In the drawings:

FIG. 7 is a front view of a mouth mask, nostril balloon, and airway in accordance with the present invention with the range of adjustment illustrated in phantom lines;

FIG. 8 is an end view of a mouth mask, nostril balloon, and airway in accordance with the present invention with a sump tube through the airway;

FIG. 9 is a top view of a mouth mask, nostril balloon, and airway in accordance with the present invention with a cover plate over the mouth mask and nostril balloon;

FIG. 10 is an end view of a mouth mask, nostril balloon, and cover plate in accordance with the present invention with a modified airway and sump tube removed from the mouth mask; and FIG. 11 is a cross-sectional view taken on the line 11—11 of FIG. 3A.

DETAILED DESCRIPTION OF THE PREFERRED EMBODIMENT

Figure 1:
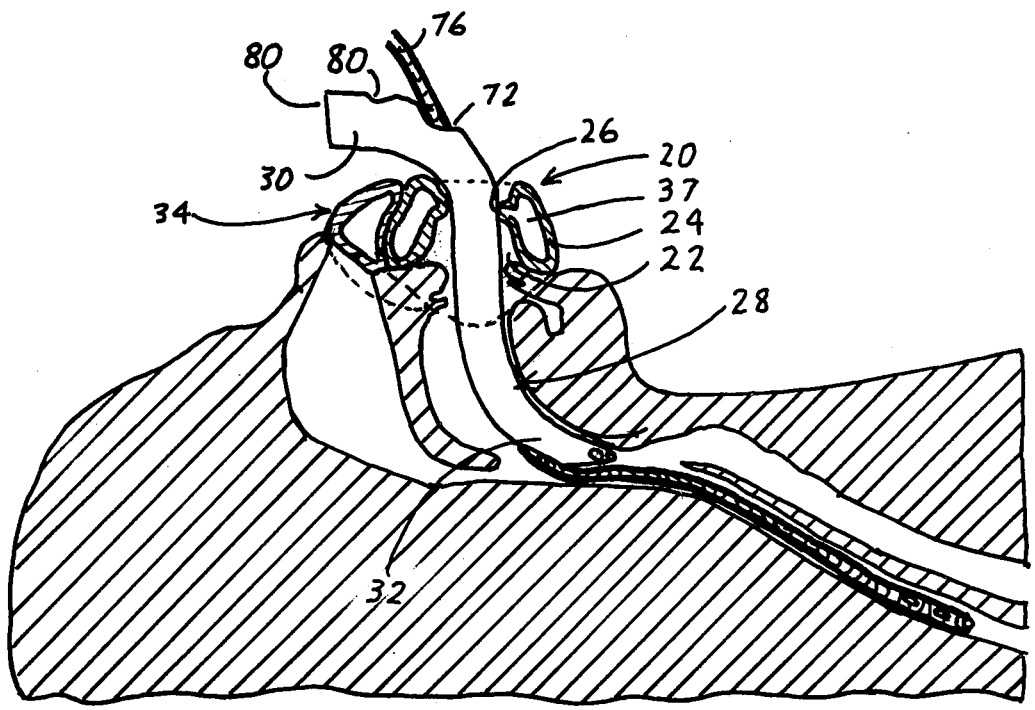
FIG. 1 is a partially cross-sectional, partially schematic view of an embodiment of the invention installed in a patient.
Figure 2A:
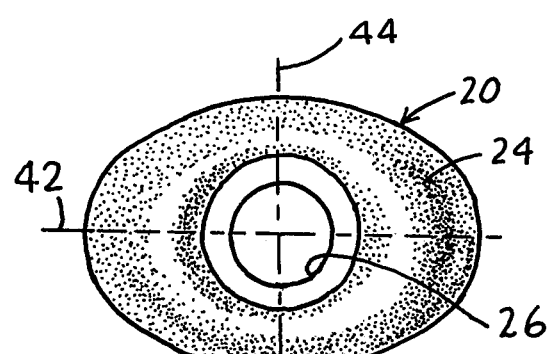
FIG. 2A is a top view of a mouth mask in accordance with the present invention.
Figure 2B:
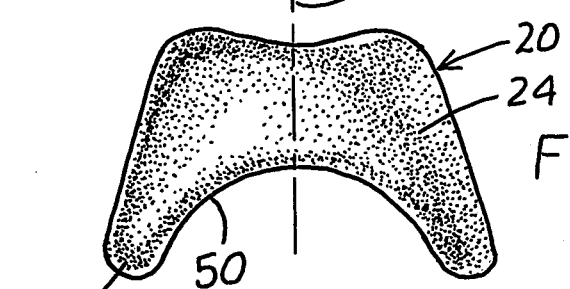
FIG. 2B is a front view of a mouth mask in accordance with the present invention.
Figure 2C:
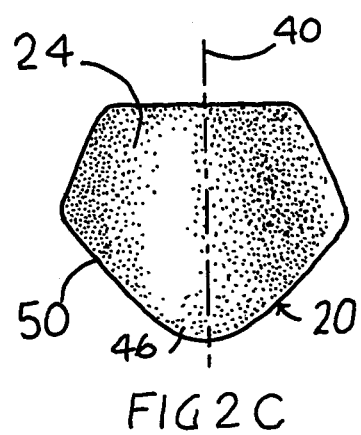
FIG. 2C is an end view of a mouth mask in accordance with the present invention.
Figure 2D:
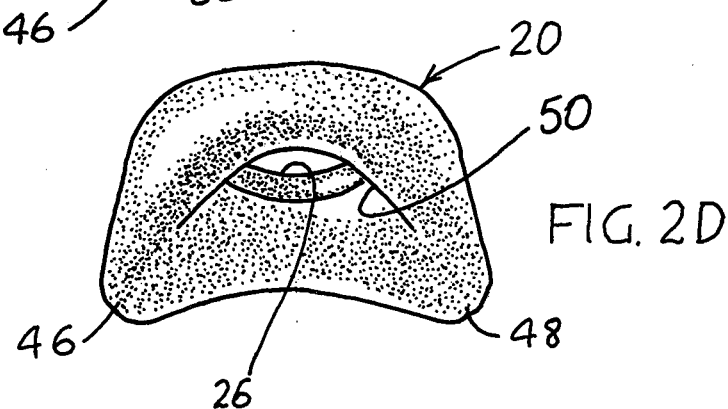
FIG. 2D is a bottom view of a mouth mask in accordance with the present invention.
Figure 3A:
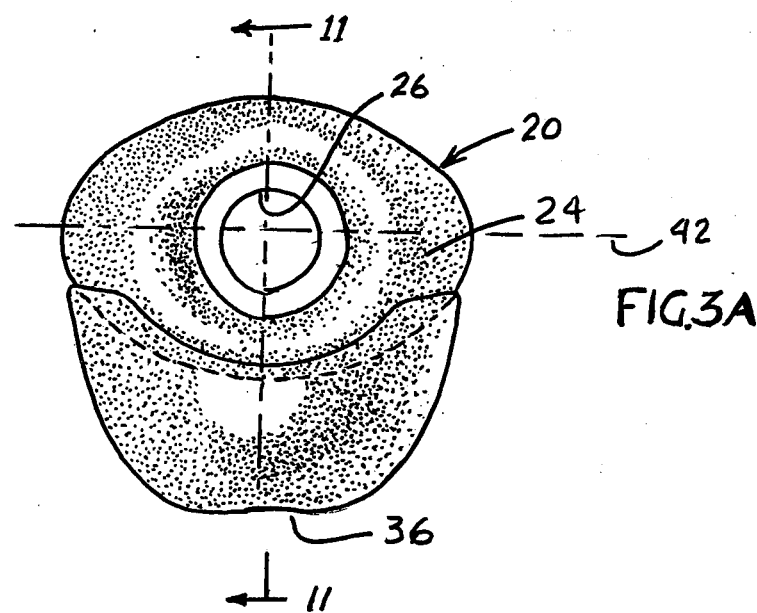
FIG. 3A is a top view of a mouth mask and nostril balloon in accordance with the present invention.
Figure 3B:
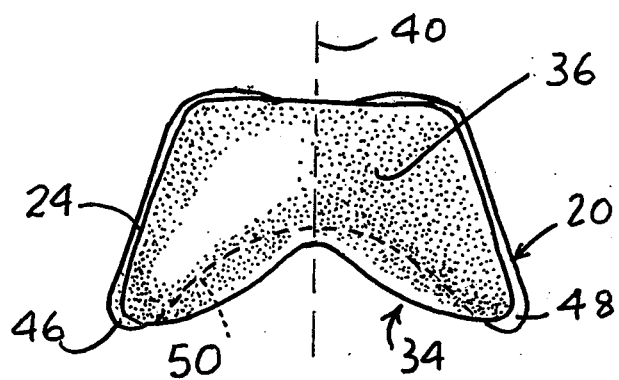
FIG. 3B is a front view of a mouth mask and nostril balloon in accordance with the present invention.
Figure 3C:
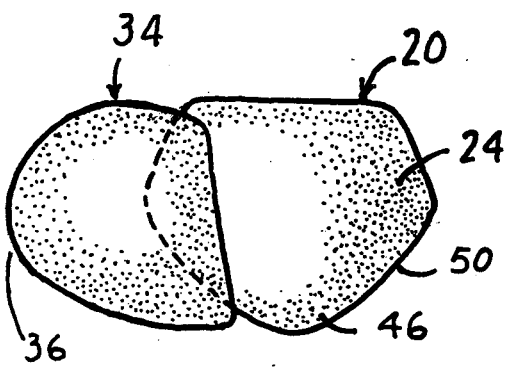
FIG. 3C is an end view of a mouth mask and nostril balloon in accordance with the present invention.
Figure 3D:
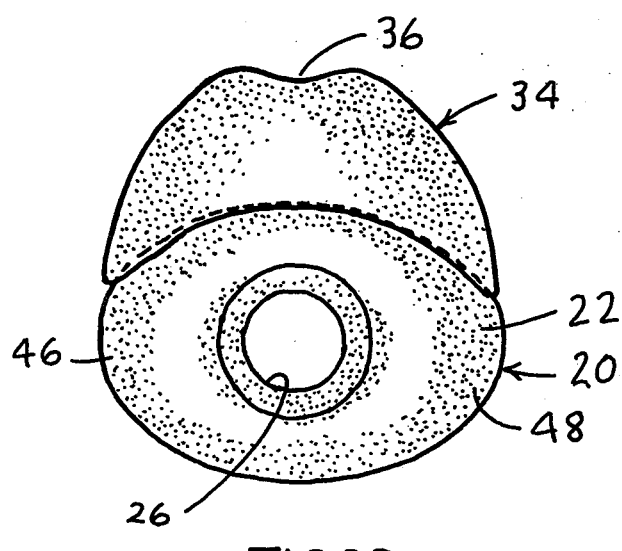
FIG. 3D is a bottom view of a mouth mask and nostril balloon in accordance with the present invention.
Figure 4A:
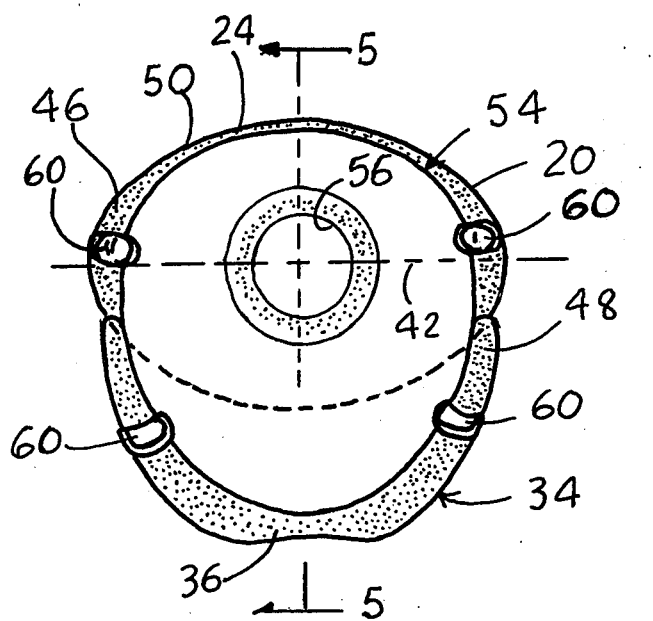
FIG. 4A is a top view of a mouth mask, nostril balloon, and cover plate in accordance with the present invention.
Figure 4B:
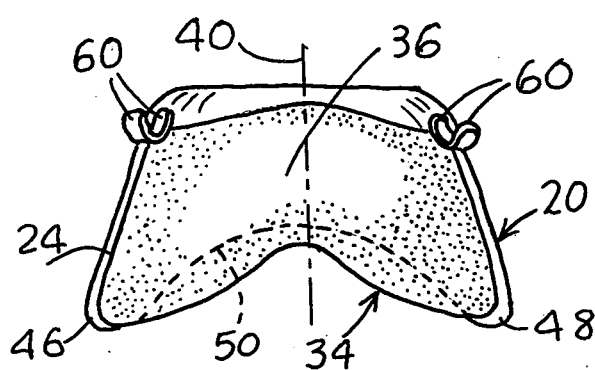
FIG. 4B is a front view of a mouth mask, nostril balloon, and cover plate in accordance with the present invention.
Figure 4C:
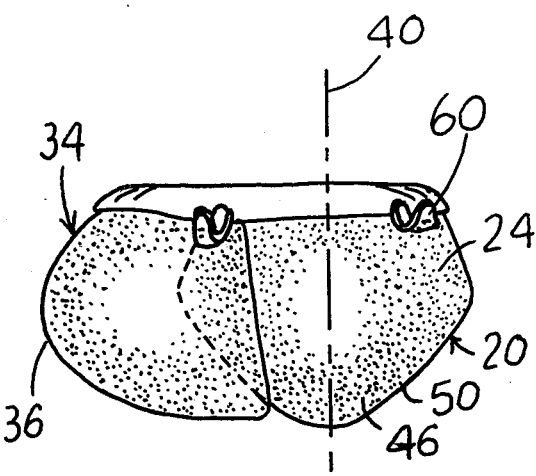
FIG. 4C is an end view of a mouth mask, nostril balloon, and cover plate in accordance with the present invention.
Figure 4D:
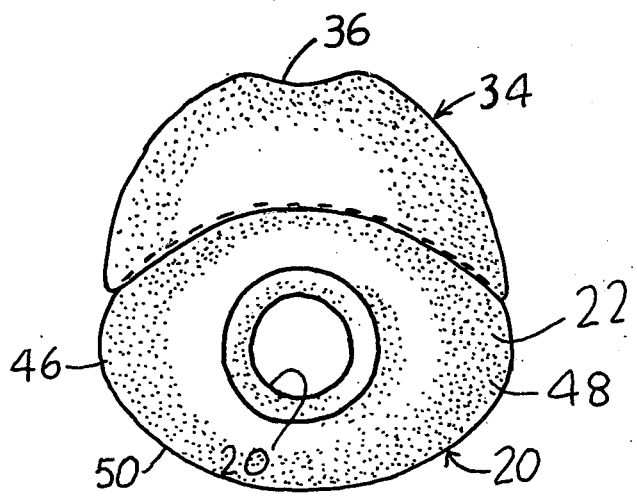
FIG. 4D is a bottom view of a mouth mask, nostril balloon, and cover plate in accordance with the present invention.

Referring to the drawings, and first to FIG. 1, the reference numeral 20 designates generally a mouth mask in accordance with the present invention. The mouth mask comprises a unitary member having an inner wall portion 22 and an outer wall portion 24. The unitary member is adapted to seal about the lips of a patient with the broad perimeter defined by the intersection of the inner and outer wall portions resting on the perioral area overlying the maxilla and mandible. The mouth mask 20 also includes an opening 26 extending through the unitary member for inserting a mouthpiece or oral airway through the unitary member for managing the patient's upper airway. The opening 26 is adapted to receive a tube 28 have a proximal end 30 disposed externally of the patient and a distal end 32 disposed internally of the patient in the region of the lower pharynx. Additionally, the mouth mask 20 may selectively be provided with nostril occluding means, such as the balloon or cushion 34, to pneumatically seal and block the nostrils of the patient.

As will be appreciated from FIG. 1, the unitary member includes a hollow cavity 37 between the wall portions 22 and 24 thereof. The unitary member can, if desired, advantageously be formed of a transparent material permitting the attending physician to visually inspect the lips of the patient, or, alternatively, the unitary member can include a filled cavity between the wall portions 22 and 24 with the fill being comprised of a soft closed cell foam material 39 (see FIG. 11) which provides a cushion support for retaining the shape of the wall portions 22 and 24. In either form, the wall portions 22 and 24 are flexible to uniformly distribute pressure to the perioral area contacted by the unitary member.

As shown in FIGS. 2A through 2D, the unitary member is generally in the form of a truncated cone with the opening 26 lying along the axis 40 of the truncated cone. The truncated cone has a cutting plane lying generally perpendicular to the axis 40 (see particularly FIG. 2C) and is shaped such that the cutting plane is generally elliptical in shape as is any plane parallel to the cutting plane. The opening 26 is concentric with the point of intersection of the major and minor axes 42 and 44, respectively, of the generally elliptical cutting plane (see FIG. 2A) and the inner wall portion 22 is inwardly concave relative to planes disposed perpendicular to the cutting plane along both the major and minor axes thereof (compare FIGS. 1, 2D and 5). The truncated cone further includes opposing lateral extensions 46 and 48 (see particularly FIG. 2B) which are spaced from one another and facing away from the cutting plane to cover the corners of the mouth of a patient. Moreover, the wall portions 22 and 24 intersect along a smooth, broad perimeter 50 generally conforming to the perioral area overlying the maxilla and mandible and extending away from the lateral extensions 46 and 48 in opposite directions toward the cutting plane along an outwardly diverging curved path (see FIGS. 1, 2B, 2C and 2D).

Referring to FIGS. 3A through 3D, the nostril occluding balloon or cushion 34 is selectively associated with the unitary member comprising the mouth mask 20. The balloon or cushion 34 is conformantly shaped to interfit with the unitary member and includes a nostril engaging surface 36 to substantially seal the nostrils of the patient. It will be appreciated that the nostril occluding balloon or cushion 34 may be maintained in position by frictional-force retention between the mouth mask 20 and the nostrils of the patient, or by other means known in the art. The balloon or cushion 34 is advantageously an inflatable-deflatable balloon which can be inflated and deflated in a fashion permitting the size thereof to be varied such that the nostril engaging surface 36 can be made to pneumatically seal the nostrils of the patient. Preferably, the inflatable-deflatable balloon includes means for inflating the balloon, such as a thickened portion 38 (see FIG. 10), formed of material capable of resealing after perforation by a hypodermic needle or, alternatively, a syringe attachment 52 (see FIG. 9) adapted to be inflated with a syringe.

Referring now to FIGS. 4A through 4D, another feature of the present invention is illustrated. It will be seen that separate means can be provided for securing the unitary member and the nostril occluding balloon in position on the patient, such as a plate 54. The plate 54 substantially covers the unitary member and the nostril occluding balloon or cushion and has an opening 56 which is alignable with the opening 26 in the unitary member. It will also be seen that the plate 54 includes means for applying pressure to the unitary member and the nostril occluding balloon or cushion to seal the lips and nostrils of the patient, such as an elastic strap 58. The elastic strip 58 (see FIG. 9) is secured to tabs 60 (see FIG. 4A) located about the perimeter of the plate 54 for positioning about the head of the patient.

Figure 5:
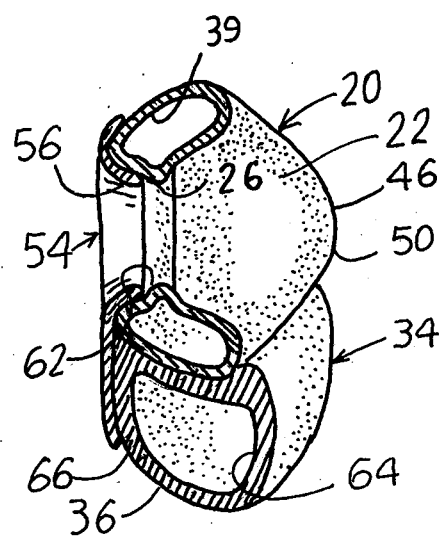
FIG. 5 is a cross-sectional view taken on the line 5—5 of FIG. 4A.

In a preferred embodiment, the plate 54 includes a pair of elastic straps 58 secured to tabs 60 located on opposite sides of plate 54 which permits one of the straps 58 to apply pressure in the region of the unitary member and the other of the straps 58 to apply pressure in the region of the nostril occluding balloon or cushion. Moreover, as shown in FIG. 5, the opening 56 in the plate 54 is defined by an integral annular collar 62 sized and shaped to fit within the opening 26 in the unitary member, and the annular collar 62 helps to maintain the plate 54 in position over the unitary member and the nostril occluding balloon during use thereof.

In an alternative embodiment, the nostril occluding means can comprise a unitary member or cushion 34' having a hollow cavity 64 defined by a self-supporting external wall portion 66 (see FIG. 11). The external wall portion 66 preferably includes a nostril engaging surface 36' to seal the nostrils of the patient, as with the earlier-described embodiment. Additionally, in this embodiment, the cavity 64 can either be hollow or optionally filled with air or a liquid such as water (not shown) or a soft closed cell foam material 68.

With the mouth mask 20 of the present invention, the tube 28 is adapted to be inserted through the opening 26 in the unitary member for attending to the patient as shown in FIG. 1. The tube 28 is a generally S-shaped airway and, as previously described, it has a proximal end 30 adapted to be disposed externally of the patient and a distal end 32 adapted to be disposed internally of the patient in the region of the lower pharynx, and it also includes a straight intermediate portion 70 with the proximal and distal ends 30 and 32, respectively, being oppositely curved. In addition, the generally S-shaped airway preferably has a generally circular cross-sectional configuration from the proximal end 30 substantially through the straight intermediate portion 70. The tube 28 also has a hole 72 in the curved proximal end portion 30 and a hole 74 in the curved distal end portion 32 and the holes 72 and 74 are substantially aligned with the straight intermediate portion 70 so that a sump tube 76 can be passed through the hole for guided insertion into the esophagus of the patient. Moreover, the generally S-shaped airway advantageously has a diameter sufficiently larger than the diameter of the sump tube 76, for instance, approximately twice as large, at least in the area of the curved proximal end portion 30 and the straight intermediate portion 70, to permit low resistance ventilation of the patient.

Referring for a moment to FIGS. 6A through 6E, the generally S-shaped airway is preferably flattened in the area of the curved distal end portion 32. It will be seen that the flattened area initially flares laterally outwardly and then tapers laterally inwardly in a generally wedge-shaped configuration. Also, the curved distal end portion 32 includes at least one hole 78 for ventilation of the patient which is located distally of the hole 74 in the distal end portion 32 permitting the sump tube 76 to be guided into the esophagus of the patient. It will be seen that the curved distal end portion 32 preferably includes a plurality of such holes 78 for ventilation of the patient. As shown, the ventilation holes 78 are located on both the anterior and posterior surfaces of the airway adjacent the distal end thereof (see FIGS. 6B and 6D).

While not clearly shown in the drawings, it is preferred that the distal end portion 32 be flattened to a dimension smaller than the diameter of the sump tube 76 to prohibit entry of the sump tube into the area of the larynx or trachea of the patient. At the other end of the generally S-shaped airway, port means such as openings 80 in the proximal end 30 are provided and the openings 80 are suitably sized and shaped so as to be adapted to be located externally of the patient, e.g., for attachment of a suction catheter and/or a ventilator and, as shown, the port means can include not only the opening in the far proximal end of the airway but also the opening through the wall of the airway in the proximal end portion thereof. With the openings 80 located generally in the proximal end portion 30, the tube 28 provides for a wide range of adjustment (as shown in FIG. 7) by means of the straight intermediate portion 70 being of a length sufficient to permit slidable adjustment of the unitary member to accommodate the variations in sizes of patients.

As will be appreciated from the drawings, the distal end portion 32 of the generally S-shaped airway is wedge-shaped, as previously described, permitting the generally S-shaped airway to be positively positioned correctly by emergency room physicians and nurses and neophyte rescuers alike. The sump tube 76 is easily inserted after positioning the airway since it merely has to be fed through the straight portion 70 of the airway and cannot inadvertently be lodged in the trachea due to the reduced anterior-posterior dimension and widened lateral dimensions of the distal end portion 32 of the airway as well as the relatively small diameter of the ventilation holes 78. Because of this arrangement, the airway is virtually foolproof.

Figure 6:
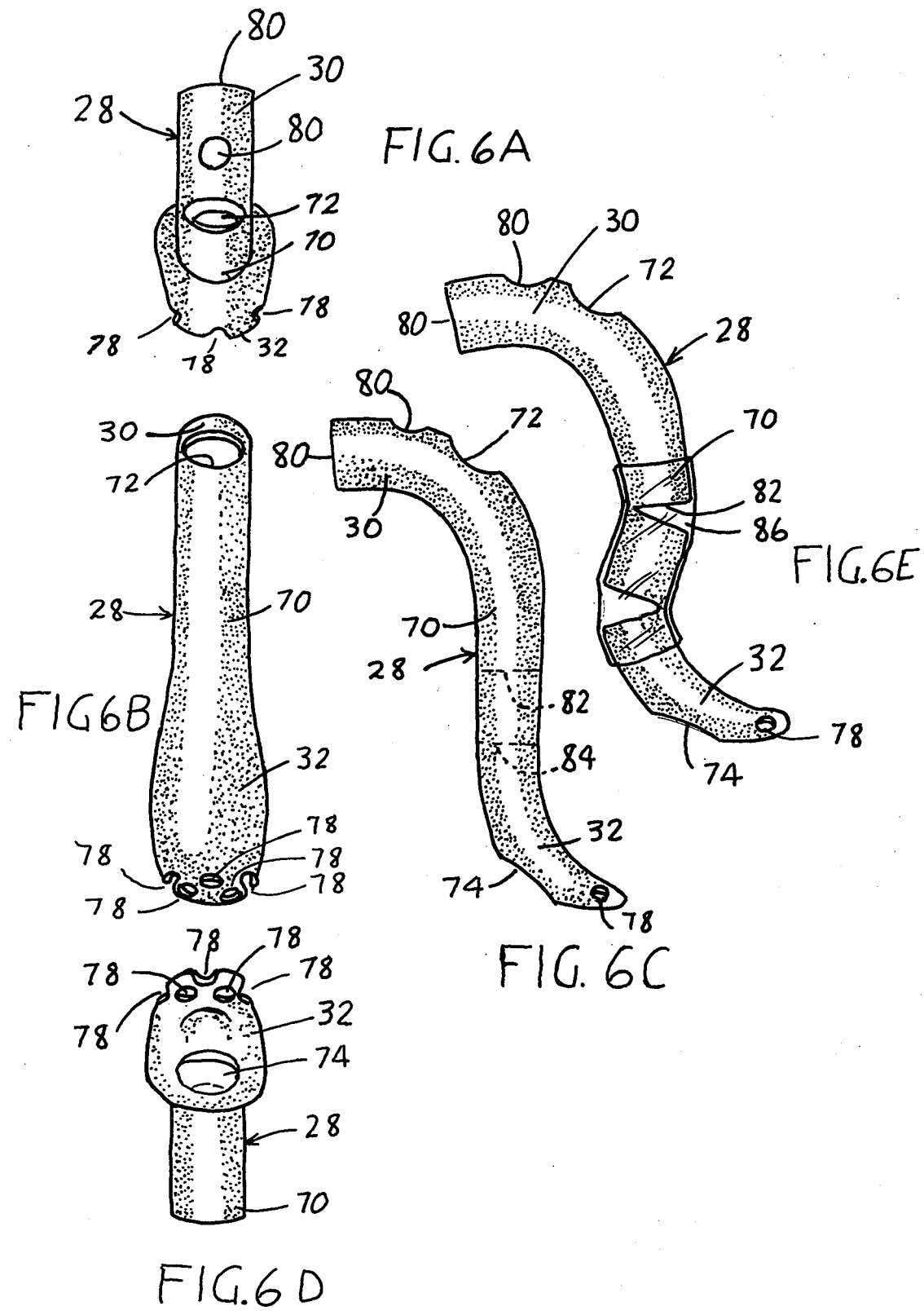
FIG. 6A is a top view of an airway in accordance with the present invention.
FIG. 6B is a front view of an airway in accordance with the present invention.
FIG. 6C is an end view of an airway in accordance with the present invention.
FIG. 6D is a bottom view of an airway in accordance with the present invention.
FIG. 6E is an end view of a modified airway in accordance with the present invention.

While the possibility of encountering a conscious patient who will not tolerate the airway is remote, the airway can be modified as shown in FIGS. 6E and 10. It will be seen that the airway 28 can be slit as at 82 and 84, substantially through the tube at longitudinally spaced locations, one of the slits extending inwardly from the anterior surface and the other of the slits extending inwardly from the posterior surface, and then covered with a sleeve 86 of, for instance, heat-shrinkable material or the like, so that the airway will, in essence, be articulated so as to be movable or bendable in the anterior and posterior directions to give added flexibility to conform to the anatomy of virtually all patients. Despite this modification, the sump tube 76 can still easily be guided into the esophagus of the patient, as before.

With the wedge-shaped structure of the distal end portion 32, the distal end portion is shaped to conform anatomically to the lower pharynx region. This not only provides the needed positive fit but also accommodates the collection of mucous by means of a suction catheter that reaches the mucous in the pharynx and can be threaded through one of the port means or holes 80 (all of which are preferably covered with a thin membrane of polyvinylchloride or silicone that can be perforated for sealing introduction of a catheter, ventilator or the like, as is the hole 72 for sealing introduction of the sump tube 76) until it reaches or passes through the hole 74 adjacent the sump tube 76. Still additional advantages of this unique construction will suggest themselves to those skilled in the art, such as the possibility of one nostril being retracted by the operator's finger for insertion of a naso-gastric tube without removing the mask.

The mouth mask of the present invention fits the widely opened mouth of the patient with an elliptical anatomical broad band perimeter with concave interfaces. The elliptical shape surrounds the widely opened mouth and rests on the broad perioral area overlying the maxilla and mandible. The mouth mask has either a hollow cavity with flexible walls or a closed-cell flexible foam structure, either of which produces a uniform distribution of pressure against the broad band of contact area on the face when the head straps are applied. The uniform pressure needed to provide a seal is low since the structure exhibits a cushion-like behavior on the patient. Moreover, because the perioral tissues are relatively thick and well-perfused, the mouth mask seals without discomfort or ischemic trauma.

The nasal occluding balloon or cushion is a separate, soft device to be wedged between the nose and mouth mask either as a separate piece or fastened to or otherwise integral with the mouth mask. It is suitably constructed either of polyurethane foam or a thin polyvinylchloride cushion and the hollow version is inflatable with air or can be filled with a liquid such as water for varying the occlusive pressure applied against the nostrils which functionally behaves like a cuff subject to inspection and readjustment to prevent leakage. With these features, the mouth mask and nostril occluding balloon or cushion are applicable without leak or discomfort by employing the cover plate and head straps previously described.

With conventional mouth masks, the major cause of failure appears to be the vast variability of the human face especially in the bridge-of-the-nose area about the oronasal perimeter. In contrast, the elliptical-convex perimeter of the wide open mouth is not only more uniform between individuals but has subcutaneous muscle and vascular supply which tolerates the prolonged application of an occlusive sealing fit. The present invention provides a mouth mask-airway-nasal cushion taking advantage of these important factors.

Various changes coming within the spirit of the present invention may suggest themselves to those skilled in the art. Hence, it will be understood that the invention is not to be limited to the specific embodiments shown and described or the uses mentioned. On the contrary, the specific embodiments and uses are intended to be merely exemplary with the present invention being limited only by the true spirit and scope of the appended claims.

I claim:
1. A mouth mask, comprising:
a unitary member having an inner wall portion, said inner wall portion being adapted to seal about the lips of a patient by resting on the perioral area overlying the maxilla and mandible, said unitary member including an outer wall portion spaced outwardly of said inner wall portion;
an opening extending through said inner and outer wall portions of said unitary member;
said inner wall portion and said outer wall portion connected to each other along their peripheral edges and the edges of said opening, said unitary member having an upper surface; and
means for occluding the nostrils of said patient, said nostril occluding means including a nostril engaging surface to substantially seal and block the nostrils of said patient, said nostril occluding means being an inflatable-deflatable cushion, said cushion having a lower surface, said cushion being inflatable and deflatable in a fashion permitting the size thereof to be varied, the lower surface of said cushion and the upper surface of said unitary member being complementary shaped to each other, whereby said cushion is wedged between said unitary member and the nostrils of said patient and said cushion being inflated to cause said nostril engaging surface to pneumatically seal and block the nostrils of said patient.

2. The mouth mask as defined in claim 1 wherein said unitary member includes a hollow cavity defined between said wall portions thereof, said wall portions being flexible to uniformly distribute pressure to the perioral area contacted by said unitary member.

3. The mouth mask as defined in claim 2 wherein said unitary member is formed of a transparent material permitting the attending physician to visually inspect the lips of said patient.

4. The mouth mask as defined in claim 1 wherein said unitary member includes a cavity defined between said wall portions thereof which is filled, said wall portions being flexible to uniformly distribute pressure to the perioral area contacted by said unitary member.

5. The mouth mask as defined in claim 4 wherein said cavity is filled with a soft closed cell foam material providing cushion support means for retaining the shape of said wall portions.

6. The mouth mask as defined in claim 1 wherein said unitary member is generally in the form of a truncated cone, said opening lying along the axis of said cone, said cone having a cutting plane lying generally perpendicular to the axis thereof.

7. The mouth mask as defined in claim 6 wherein said cone is shaped such that said cutting plane is generally elliptical in shape, said cone also being shaped such that any plane parallel to said cutting plane is also generally elliptical in shape.

8. The mouth mask as defined in claim 7 wherein said opening is concentric with the point of intersection of the major and minor axes of said generally elliptical cutting plane.

9. The mouth mask as defined in claim 8 wherein said inner wall portion is inwardly concave relative to planes disposed perpendicular to said cutting plane along both the major and minor axes thereof.

10. The mouth mask as defined in claim 9 wherein said unitary member includes opposing lateral extensions spaced from one another and facing away from said cutting plane to cover the corners of the mouth of a patient.

11. The mouth mask as defined in claim 10 wherein said wall portions intersect along a smooth perimeter conforming to the perioral area overlying the maxilla and mandible, said smooth perimeter extending toward said lateral extensions in opposite directions toward said cutting plane along an outwardly diverging curved path.

12. The mouth mask as defined in claim 1 wherein said nostril occluding means includes means for inflating said cushion, said cushion inflating means including a thickened portion of said cushion formed of material capable of resealing after perforation by a hypodermic needle.

13. The mouth mask as defined in claim 1 wherein said nostril occluding means includes means for inflating said cushion, said cushion inflating means including syringe attachment means for inflation by a syringe.

14. The mouth mask as defined in claim 1 including means for securing said unitary member and said nostril occluding means in position on said patient.

15. The mouth mask as defined in claim 14 wherein said securing means includes a plate substantially covering said unitary member and said nostril occluding means, said plate having an opening therein alignable with said opening in said unitary member, said plate including means for applying pressure to said unitary member and said nostril occluding means to seal the lips and nostrils of said patient.

16. The mouth mask as defined in claim 15 wherein said opening in said plate is defined by an annular collar sized and shaped to fit within said opening in said unitary member, said annular collar helping to maintain said plate in position over said unitary member and said nostril occluding means during use thereof.

17. The mouth mask as defined in claim 15 wherein said means for applying pressure to said unitary member and said nostril occluding means includes at least one elastic strap secured to said plate adapted to be positioned about the head of said patient.

18. The mouth mask as defined in claim 17 wherein said elastic strap is secured to said plate on opposite sides thereof adjacent said unitary member, said plate including a second elastic strap secured thereto adjacent said nostril occluding means.

19. The mouth mask as defined in claim 1 wherein said nostril occluding means is a unitary member means having an exterior wall portion including said nostril engaging surface to seal and block the nostrils of said patient, said exterior wall portion defining a hollow cavity.

20. A mouth mask comprising:
a unitary member having an inner wall portion, said inner wall portion being adapted to seal about the lips of a patient by resting on the perioral area overlying the maxilla and mandible, said unitary member including an outer wall portion spaced outwardly of said inner wall portion;
an opening extending through said inner and outer wall portions of said unitary member;
said inner wall portion and said outer wall portion connected to each other along their peripheral edges and the edges of said opening, said unitary member having an upper surface; and
means for occluding the nostrils of said patient, said nostril occluding means including a nostril engaging surface to substantially seal and block the nostrils of said patient, said nostril occluding means being a unitary member means having an exterior wall portion including an upper surface defining said nostril engaging surface to seal and block the nostrils of said patient and a lower surface, said exterior wall portion defining a cavity which is filled, the lower surface of said unitary member means and the upper surface of said unitary member being complementary shaped to each other, whereby said unitary member means is wedged between said unitary member and the nostrils of said patient.

21. A mouth mask, comprising:
a unitary member having an inner wall portion, said inner wall portion being adapted to seal about the lips of a patient by resting on the perioral area overlying the maxilla and mandible, said unitary member including an outer wall portion spaced outwardly of said inner wall portion;
an opening extending through said inner and outer wall portions of said unitary member;
said inner wall portion and said outer wall portion connected to each other along their peripheral edges and the edges of said opening; and
a tube adapted to be inserted through said opening in said unitary member for the purpose of ventilating and managing the upper airway of said patient, said tube being a generally S-shaped airway having a proximal end adapted to be disposed externally of said patient and a distal end adapted to be disposed internally of said patient in the region of the lower pharynx, said generally S-shaped airway having a generally straight intermediate portion with oppositely curved proximal and distal end portions, said generally S-shaped airway having a hole in said curved proximal end portion and a hole in said curved distal end portion, said holes being substantially aligned with said straight intermediate portion, and including a sump tube adapted to be passed through said holes for guided insertion into the esophagus of said patient.

22. The mouth mask as defined in claim 21 wherein said generally S-shaped airway has a circular cross-sectional configuration from said proximal end substantially through said straight intermediate portion.

23. The mouth mask as defined in claim 21 wherein said generally S-shaped airway has a dimension sufficiently larger than the dimension of said sump tube in the area of said curved proximal end portion and said straight intermediate portion to permit low resistance ventilation of said patient.

24. The mouth mask as defined in claim 21 wherein said generally S-shaped airway is flattened in the area of said curved distal end portion, said flattened area initially flaring laterally outwardly and then tapering laterally inwardly in a generally wedge-shaped configuration.

25. The mouth mask as defined in claim 21 wherein said curved distal end portion includes a plurality of holes for ventilation of said patient located distally of said hole in said distal end portion permitting said sump tube to be guided into the esophagus of said patient.

26. The mouth mask as defined in claim 21 wherein said curved distal end portion includes a plurality of holes for ventilation of said patient, said ventilation holes being located on both the anterior and posterior surfaces of said airway adjacent said distal end thereof.

27. The mouth mask as defined in claim 26 wherein said distal end portion is flattened to a dimension smaller than the diameter of the sump tube to prohibit entry of said sump tube into the area of the larynx or trachea of said patient.

28. The mouth mask as defined in claim 26 wherein said ventilation holes are smaller in diameter than the diameter of said sump tube to prohibit entry of said sump tube into the area of the larynx or trachea of said patient.

29. The mouth mask as defined in claim 21 wherein said generally S-shaped airway includes port means associated with said proximal end thereof, said port means being adapted to be located externally of said patient for attachment of a suction catheter and a ventilator.

30. The mouth mask as defined in claim 21 wherein said straight intermediate portion is of a length sufficient to permit slidable adjustment of said unitary member to accommodate the variations in sizes of patients.

31. The mouth mask as defined in claim 21 in which said straight intermediate portion of said generally S-shaped airway includes a pair of slits disposed at longitudinally spaced locations, one of said slits extending substantially through said airway from the anterior surface thereof and the other of said slits extending substantially through said airway from the posterior surface thereof, said straight intermediate portion of said generally S-shaped airway being covered with a sleeve of heat-shrinkable material.

32. An airway adapted to traverse a mouth mask with an opening therethrough, comprising:
a tube adapted to be inserted through the opening in said mouth mask and having a proximal end adapted to be disposed externally of said patient and a distal end adapted to be disposed internally of said patient in the region of the lower pharynx, said tube comprising a generally S-shaped airway having a generally straight intermediate portion with oppositely curved proximal and distal end portions, said generally S-shaped airway having a hole in said curved proximal end portion and a hole in said curved distal end portion, said holes being substantially aligned with said straight intermediate portion, and including a sump tube adapted to be passed through said holes for guided insertion into the esophagus of said patient.

33. The airway as defined in claim 32 wherein said generally S-shaped airway has a circular cross-sectional configuration from said proximal end substantially through said straight intermediate portion.

34. The airway as defined in claim 32 wherein said generally S-shaped airway has a dimension sufficiently larger than the dimension of said sump tube in the area of said curved proximal end portion and said straight intermediate portion to permit low resistance ventilation of said patient.

35. The airway as defined in claim 32 wherein said curved distal end portion includes at least one hole for ventilation of said patient located distally of said hole in said distal end portion permitting said sump tube to be guided into the esophagus of said patient.

36. The airway as defined in claim 32 wherein said curved distal end portion includes a plurality of holes for ventilation of said patient, said ventilation holes being located on both the anterior and posterior surfaces of said airway adjacent said distal end thereof.

37. The airway as defined in claim 36 wherein said distal end portion is flattened to a dimension smaller than the diameter of said sump tube to prohibit entry of said sump tube into the area of the larynx or trachea of said patient.

38. The airway as defined in claim 36 wherein said ventilation holes are smaller in diameter than the diameter of said sump tube to prohibit entry of said sump tube into the area of the larynx or trachea of said patient.

39. An airway adapted to traverse a mouth mask, with an opening therethrough comprising:
a tube adapted to be inserted through the opening in said mouth mask and having a proximal end adapted to be disposed externally of said patient and a distal end adapted to be disposed internally of said patient in the region of the lower pharynx, said tube comprising a generally S-shaped airway having a generally straight intermediate portion with oppositely curved proximal and distal end portions, said generally S-shaped airway being flattened in the area of said curved distal end portion, said flattened area initially flaring laterally outwardly and then tapering laterally inwardly in a generally wedge-shaped configuration.

40. The airway as defined in claim 39 wherein said generally S-shaped airway includes port means associated with said proximal end thereof, said port means being adapted to be located externally of said patient for attachment of a suction catheter and a ventilator.

41. The airway as defined in claim 39 wherein said straight intermediate portion is of a length sufficient to permit slidable adjustment of said unitary member to accommodate the variations in sizes of patients.

42. An airway adapted to traverse a mouth mask with an opening therethrough, comprising:
a tube adapted to be inserted through the opening in said mouth mask and having a proximal end adapted to be disposed externally of said patient and a distal end adapted to be disposed internally of said patient in the region of the lower pharynx, said tube comprising a generally S-shaped airway having a generally straight intermediate portion with oppositely curved proximal and distal end portions, said straight intermediate portion of said generally S-shaped airway including a pair of slits disposed at longitudinally spaced locations, one of said slits extending substantially through said airway from the anterior surface thereof and the other of said slits extending substantially through said airway from the posterior surface thereof, said intermediate portion of said generally S-shaped airway being covered with a sleeve of heat-shrinkable material.

43. An airway adapted to traverse a mouth mask with an opening therethrough, comprising:
a tube adapted to be inserted through the opening in said mouth mask and having a proximal end adapted to be disposed externally of said patient and a distal end adapted to be disposed internally of said patient in the region of the lower pharynx, said tube comprising a generally S-shaped airway having a generally straight intermediate portion with oppositely curved proximal and distal end portions, said generally S-shaped airway having a hole in said curved proximal end portion and a hole in said curved distal end portion, said holes being substantially aligned with said straight intermediate portion and including a sump tube adapted to be passed through said holes for guided insertion into the esophagus of said patient, said generally S-shaped airway also including port means associated with said proximal end thereof adapted to be located externally of said patient for attachment of a suction catheter and a ventilator, said hole in said curved proximal end portion and said port means associated with said curved proximal end portion being covered by a thin membrane capable of being perforated for sealingly introducing said sump tube, suction catheter and ventilator.

* * * * *